United States Patent [19]

Kaplan et al.

[11] Patent Number: 5,231,001

[45] Date of Patent: Jul. 27, 1993

[54] TRK TYROSINE KINASE RECEPTOR IS THE PHYSIOLOGICAL RECEPTOR FOR NERVE GROWTH FACTOR

[75] Inventors: David Kaplan, Middletown, Md.; Dionisio Martin-Zanca, Salamanca, Spain; Luis F. Parada, Frederick, Md.

[73] Assignee: The United States of America as represented by the Department of Health and Human Services, Washington, D.C.

[21] Appl. No.: 668,298

[22] Filed: Mar. 14, 1991

[51] Int. Cl.$^5$ .......................................... G01N 33/567
[52] U.S. Cl. .................... 435/7.21; 435/7.4; 435/15; 435/194; 436/536; 530/399
[58] Field of Search ............... 530/399, 835; 435/15, 435/193, 240.2, 244, 7.21, 971, 968; 436/518, 519, 536, 811

[56] References Cited

PUBLICATIONS

Hempstead et al., "Expression of Functional Nerve Growth Factor Receptors After Gene Transfer", Science, vol. 243, Jan. 20, 1989, pp. 373–375.
Maher et al., "Nerve Growth Factor induces protein tyrosine phosphorylation", Proc. Nat'l Acad. Sci. USA, vol. 85, Sep. 1988, pp. 6788–6791.
Martin-Zanca et al., "Molecular and Bio. Chemical Characterization of the Human TRK Proto-Oneogene", Mole & Cellar Bio, vol. 9, No. 1, Jan. 1989, pp. 24–33.
Lazarovici et al., "Long Terms, Heterologous Down Regulation of Epidermal Growth Factor Receptor in PC12 Cells lay Nerve Growth Factor", Journal Cell Biology vol. 104, 1987, pp. 1611–1621.
Taniuchi et al.,*The Journal of Biological Chemistry* 261(28):13342 (1986).
Kaplan, et al., *Science* 252:554 (1991).
Hempstead et al., *Nature* 350:678 (1991).
Ross et al., *PNAS USA* 81:6681 (1984).
Chandler et al., *J. Biol. Chem.* 259:6882 (1984).
Birren et al., *Science* 257:395 (1992).
Vetter et al., *PNAS USA* 88:8650 (1991).
Kaplan et al., *Nature* 6314:158 (1991).

*Primary Examiner*—Esther L. Kepplinger
*Assistant Examiner*—Donna C. Wortman
*Attorney, Agent, or Firm*—Foley & Lardner

[57] ABSTRACT

The present invention relates to a complex comprising nerve growth factor (NGF) and trk-proto-oncogene protein. The present invention also relates to methods for detecting the presence of NGF and trk-proto-oncogene receptor. The present invention further relates to methods that may be used in diagnostics and therapeutics for neurodegenerative diseases such as Alzheimer's and Huntington's by detecting NGF-trk receptor pairs.

5 Claims, 7 Drawing Sheets

FIG. 1A
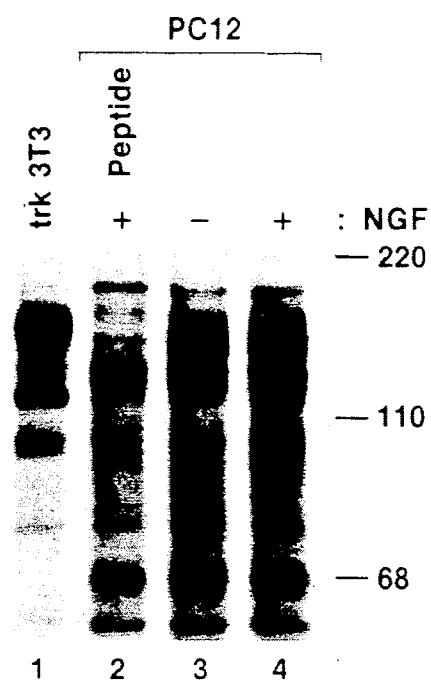
FIG. 1B
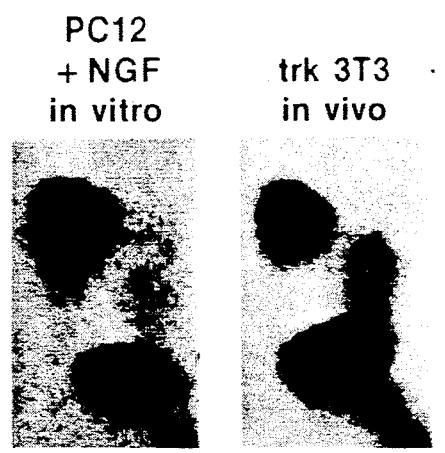
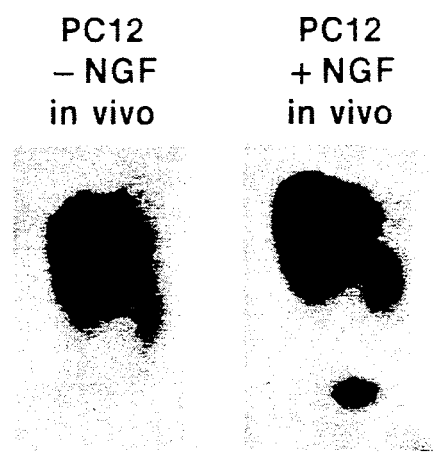
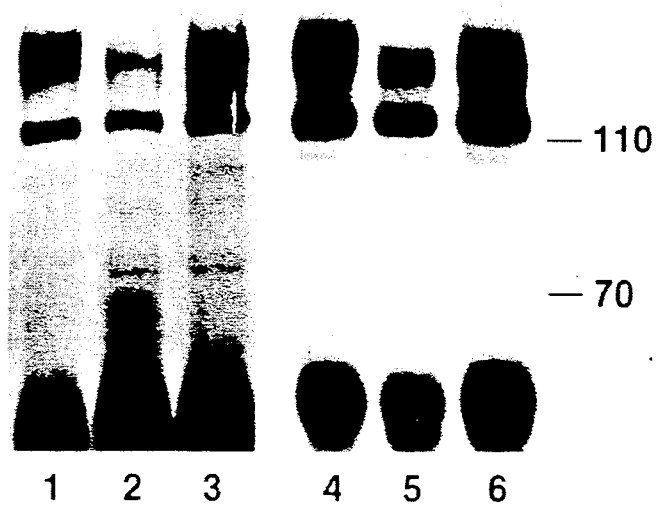
FIG. 1C

FIG. 3A
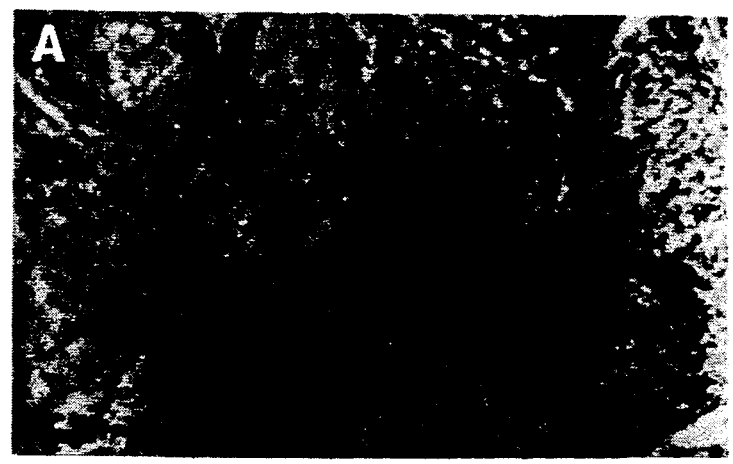
FIG. 3B

TRK TYROSINE KINASE RECEPTOR IS THE PHYSIOLOGICAL RECEPTOR FOR NERVE GROWTH FACTOR

FIELD OF THE INVENTION

The present invention relates to a complex comprising the neurotrophic factors nerve growth factor (NGF) and trk-proto-oncogene protein. The present invention also relates to methods for detecting the presence of NGF ligand, and trk-proto-oncogene receptor protein.

The present invention further relates to methods of diagnosing and treating conditions of nerve growth disease and regeneration such as Alzheimer's disease and neuroblastoma. In particular the present method involves detection of the ligand receptor pairs.

The present invention further relates to methods for detecting neurotrophic factor receptor/ligand complexes on the basis of structural and functional relatedness to trk and NGF.

BACKGROUND OF THE INVENTION

The development of the vertebrate nervous system is characterized by a series of complex events beginning with an apparently homogeneous neuroepithelium in the early embryo and leading to formation of diverse, highly ordered, and interconnected neural cell types in the adult. Considerable descriptive and experimental evidence has been amassed which points to the existence of limiting diffusible factors that are required for the targeting, survival, and proper synaptic arrangement of neurons (R. W. Oppenheim, In: Studies in Developmental Neurobiology. (Cowan, W. M. ed.), Oxford Univerity Press, pp. 74-133, 1981; W. D. Snider and E. M. Johnson, Ann. Neurol. 26:489-506 (1989)). Functional neuronal circuits are sculpted from an initially overabundant production of neurons during development. In the mid term embryo, a process of programmed cell death eliminates a major proportion of the neuron population, leaving behind the appropriate number of neurons required for innervation of target tissues (V. Hamburger and R. Levi-Montalcini, J. Exp. Zool. 111:457-502 (1949); Y.-A. Barde, Neuron 2:1525-1535 (1989)).

The discovery of Nerve Growth Factor (NGF) provided the first direct evidence for the existence of neurotrophic, polypeptide factors (R. Levi-Montalcini and V. Hamburger, J. Exp. Zool. 116:321-362 (1951); R. Levi-Montalcini and P. U. Angeletti, Physiol. Rev. 48:534-569(1968)). This has been followed by the more recent description of additional neurotrophic factors: BDNF, CTNF, and NT-3, (for review see W. D. Snider and E. M. Johnson, Ann. Neurol. 26:489-506 (1989); G. Barbin et al., J. Neurochem. 43:1468-1478 (1984); P. C. Maisonpierre et al., Science 247:1446-1451 (1990)). The physiological consequences elicited by NGF in vitro and in vivo have been at the center of research in neurobiology for several decades. Consequently, considerable information is now available about the cell types that respond to NGF in the peripheral and central nervous systems.

NGF is known to play a role in the targeting and survival of sympathetic and neural crest-derived sensory neurons as well as in selected populations of cholinergic neurons in the brain (L. A. Greene and E. M. Shooter, Annu. Rev. Neurosci. 3:353-402 (1980); H. Thoenen and Y.-A. Barde, Physiol. Rev. 60:1284-1335 (1980); H. Gnahn et al., Dev. Brain. Res. 9:45-52 (1983)). It appears that the NGF dependent cholinergic neurons in the basal forebrain correspond to the population of cells that undergo attrition of Alzheimer's disease (F. Hefti, Annals of neurology, 13:109-110 (1983); Hefti and Wemer, 1986; Johnson and Tanuchi, 1987; P. J. Whitehouse et al., Science 215:1237-1239 (1982)). In vivo studies, in which NGF was injected in the periphery of the mouse embryo trunk, result in enhanced survival of sensory ganglia that are normally targeted for cell death (V. Hamburger et al., J. Neurosci. 1:60-71 (1981); I. B. Black et al., In: Growth Factors and Development, Current Topics in Developmental Biology, vol. 24 (Nilsen-Hamilton, ed.), pp. 161-192 (1990)).

Exposure of embryos to NGF antibodies results in reduced survival of dorsal root ganglion neurons while injection of NGF antibodies into neonate mice has the principal effect of inhibiting the survival of sympathetic neurons (R. Levi-Montalcini and B. Booker, Proc. Natl. Acad. Sci. USA, 46:373-384 or 384-391 (1960); S. Cohen, Proc. Natl. Acad. Sic. USA, 46:302-311 (1960); E. M. Johnson et al., Science 210:916-918 (1980)).

In vitro, some tumor cell lines of neural origin respond to the presence of NGF by undergoing differentiation along neuronal pathways. PC12 cells, derived from a rat pheochromocytoma, are the best characterized of these cell lines and represent a widely accepted model for NGF-mediated response and for neuronal differentiation (L. A. Greene and A. S. Tischler, Proc. Natl. Acad. Sci. USA 73:2424-2428 (1976)).

Although much is understood about the biology of NGF outside the cell, the mechanisms by which NGF elicits neurotrophic effects within the cell have not been fully resolved. Interaction of NGF with a cell receptor is a requisite step in the transmission of neurotrophic signals within the cell (for review see M. V. Chao, In: Handbook of Experimental Pharmacology, vol. 95/II Peptide Growth Factors and Their Receptors II (Sporn, M. B. and Roberts, A. B. eds.), Springer-Verlag, Heidelberg, pp. 135-165 (1990)). A major advance in understanding NGF interactions with the cells was the identification and cloning of a 75kDa receptor (75kNGF-R) that binds NGF, and is present in NGF-responsive cells. The clones of the gene encoding 75kNG-R have been characterized from several species (M. V. Chao et al., Science 232:418-421 (1986); M. J. Radeke et al., Nature 325:593-597 (1987)). Unfortunately, the structural and biological properties of 75kNGF-R have provided limited clues about the nature of the NGF signal trandsuction pathway inside the cell. 75kNGF-R displays the binding properties of a low affinity NGF receptor (Kd$\approx 10^{-9}$M) when expressed in exogenous cell lines and analysis of the intracellular domain has not revealed putative domains of catalytic action (M. V. Caho, In: Handbook of Experimental Pharmacology, Vol. 95/II Peptide Growth Factors and Their Receptors II (Sporn, M. B. and Roberts, A. B. eds.), Springer-Verlag, Heidelberg, pp. 135-165 (1990)).

The biological responsiveness to NGF, however, is widely held to depend upon interactions with a high affinity binding component implying that other receptor or receptor subunits may be involved in NGF responses. The search for potential second messengers that might transmit NGF signals in PC12 cells has led to recent evidence indicating that activation of tyrosine kinases may represent an early response to the presence of NGF (Maher 1988). These data implicate tyrosine kinases as candidates in the composition of a high affinity receptor.

The trk proto-oncogene encodes a tyrosine kinase (TK) receptor with a tightly regulated neural pattern of expression during murine development (D. Martin-Zanca et al., *Genes Dev.* 4:683–694 (1990); D. Martin-Zanca et al., In: The Avian Model in Developmental Biology: From Organism to Genes, Editions du CNRS - 1990, pp. 291-302 (1990)). In vivo, transcripts for this gene were observed only in neural crest-derived sensory neurons of the peripheral nervous system through E17 of mouse development. Several lines of evidence have led applicants to investigate the possible involvement of trk in pC12 cell NGF-mediated events.

The need exists in the field to determine whether trk proto-oncogene tyrosine kinase receptor is activated via direct interaction with NGF. The present invention provides a complex comprising NGF ligand and trk-proto-oncogene receptor. The direct binding of NGF to the trk receptor leads to tyrosine phosphorylation and tyrosine kinase activity in response to NGF exposure in trk expressing cells. Knowledge of the trk physiological receptor and cognate NGF complex may allow a detailed study of nerve growth and regeneration. Furthermore, the demonstration of NGF-trk receptor complexes demonstrates methods for identifying related tyrosine kinase receptors providing additional neurotropic-factor pairs.

SUMMARY OF THE INVENTION

It is an object of the present invention to provide a complex comprising a nerve growth factor (NGF) ligand and trk-proto-oncogee protein receptor and methods of utilizing the complex.

In one embodiment the present invention relates to a complex of NGF and trk-proto-oncogene receptor protein wherein said complex is free of protein with which it is naturally associated.

In another embodiment the present invention relates to a complex comprising a NGF ligand and trk-proto-oncogene receptor protein wherein one member of said complex is bound to a solid support.

In yet another embodiment the present invention relates to a method of detecting the NGF:trk-proto-oncogene receptor protein complex in a sample comprising reacting said sample with an antibody that binds specifically with either NGF or trk-proto-oncogene receptor protein on the complex. A positive immunological reaction is indicative of the presence of the complex in the sample.

In a further embodiment, the present invention relates to a method of diagnosing degenerative neuronal diseases in a patient suspected of having the disease comprising reacting a biological sample from the patient with an antibody that binds with NGF:trk-proto-oncogene receptor protein complex.

In yet another embodiment, the present invention relates to a method of diagnosing a tissue undergoing neuronal regeneration in a patient comprising reacting a biological sample from the patient with an antibody that binds to a NGF:trk-proto-oncogene receptor protein complex.

A further embodiment of the present invention relates to a method of diagnosing a disease state in the patient suspected of having the stated disease comprising reacting a biological sample from the patient with an antibody that binds to a trk NGF:trk-proto-oncogene receptor protein complex.

In another embodiment, the present invention relates to a method for detecting NGF in a sample comprising contacting the sample with trk-proto-oncogene receptor protein under conditions such that binding of NGF present in the sample to the receptor is effected and detecting the presence of bound NGF.

In a further embodiment the present invention relates to a method for detecting trk-proto-oncogene receptor protein in a sample comprising the steps of contacting the same with NGF under conditions such that binding of said receptor present in the sample to NGF is effected and detecting the presence of bound receptor.

Various other objects and advantages of the present invention will become apparent from the drawings and the following description of the invention.

The entire contents of all publications mentioned herein are incorporated by reference.

BRIEF DESCRIPTION OF THE DRAWINGS

FIG. 1 shows the tyrosine phosphorylation of p140trk in PC12 cells and trk-expressing NIH-3T3 cells treated with NGF. 1a,p140trk immunoprecipitated from PC12 cells or trk-expressing 3T3 cells labeled with $^{32}$P-orthophosphate. Immunoprecipitaes were prepared with rabbit anti-trk antisera 43-4 (D. Martin-Zanca et al., *Mol. Cell. Biol.* 9:24–33 (1988)) from lysates prepared from 3T3 cells expressing the rat trk gene (trk 3T3) (lane 1) or PC12 cells treated for 5 min with 100 ng/ml NGF at 37° C. (lanes 2 and 4) or mock treated (lane 3). The immunoprecipitate shown in lane 2 was prepared in the presence of the peptide used to generate the rabbit 43-4 trk antibody (Martin-Zanca et al. 1988). Shown in 1b is the phosphoamino acid analysis of trk proteins phosphorylated in vitro in p140trk immunoprecipitates from NGF treated PC12 cells in vivo from NGF treated (+) or untreated (−) PC12 cells, or in vivo from trk3T3 cells. The positions of phosphoserine (S), phosphothreonine (T), and phosphotyrosine (Y) are indicated. 1c, trk proteins from trk 3T3 cells phosphorylated in vivo or in vivo. In lanes 1-3, p140trk immunoprecipitates were probed with P-tyr antibodies. In lanes 4-6, p140trk proteins were phosphorylated in vitro in kinase assays. Cells were treated with suramin (lanes 2 and 5) or with 500 ng/ml NGF for 10 min following suramin treatment. The band migrating at 110 kDa is a glycosylation precursor of p140$^{prototrk}$ (Martin-Zanca et al. 1988). The band at the bottom of the figure is IgG. Molecular weight markers in kDa are indicated.

rtrk 3T3 cells were generated by CaPO$_4$ mediated transfection of a rat trk cDNA into NIH-3T3 cells. Rat trk cDNAs were obtained from an embryonic rat DRG cDNA library kindly provided by M. C. Fishman. The longest trk cDNA obtained (2.4 kbp) was missing approximately 150 bp of the coding region as compared to available mouse and human trk sequence. The missing bases plus minimal (~50 bp) 5' flanking non-coding sequences were replaced from mouse first coding exon sequences and the reconstructed gene was placed downstream of an MSV-LTR. PC12 cells or rtrk 3T3 cells (2×10$^7$) were labeled with $^{32}$P orthophosphate (1 mCi.ml in 4 ml) for 4 hr at 37° C. Cells were treated with NGF for the indicated times, washed, lysed in buffer containing 1% NP40, and the lysates immunoprecipitated with trk antibody 43-4 (Kaplan et al., *Cell* 61:125–133 (1990)) and electrophoresed on 7.5% SDS-PAGE gels as previously described (Kaplan et al., 1990). For 1b, the phosphorylated trk bands were eluted from the gel and phosphoamino acid analysis performed as described (B. M. Sefton et al., *J. Cell* 24:165-174 (1981). p140trk protein from NGF treated PC12 cells was phosphorylated in vitro. For 1c, rtrk 3T3 cells were treated with 1 mM suramin in Dulbecco's Modified Eagle Medium (DMEM) for 2h or mock treated. Following extensive washing of the cells with DMEN, NGF was added for the time indicated. Cells were lysed and the lysates were immunoprecipitated with trk antibody. Immunoprecipitates were either subjected to immunoblot analysis with the phosphotyrosine (Ptyr) monoclonal antibody 4G10 (Lanes 1-3), or were analyzed in kinase assays. (Morrison, et al., *Cell* 58:649-657 (1989) and Kaplan et al. 1990) Similar amounts of trk protein were present in each lane.

FIG. 2. Time course, growth factor specificity, and dose response of trk tyrosine phosphorylation in PC12 cells. A, Time course of trk tyrosine phosphorylation. Cells ($2 \times 10^7$) were treated with 50 ng/ml NGF at 37° C. B, Effects of growth and differentiation factors on trk tyrosine phosphorylation. Cells were treated with 100 ng/ml NGF, 100 ng/ml basic fibroblast growth factor (FGF) (Boehringer Mannheim Biochemicals), 100 ng/ml epidermal growth factor (EGF) (Upstate Biotechnology, Inc.), 100 nM insulin (Signman), or 1 $\mu$g/ml phorbal 12-myristate 12-acetate (PMA) (Sigma) for 15 min. at 37° C. C, dose response of trk tyrosine phosphorylation. Cells were treated for 30 min. at 37° C. with increasing concentrations of NGF. Shown are Western blot analysis with Pryr antibodies of trk immunoprecipitates prepared with trk antibody 43-4.

FIG. 3 represents the trk expression in day 17 mouse embryo DRGs. A, Brightfield and B, darkfield optics of a sagittal section through the thoracic region of an E17 embryo. In situ protocols and probes have been described in detail elsewhere (Martin-Zanca et al. 1990).

Figure 4A:
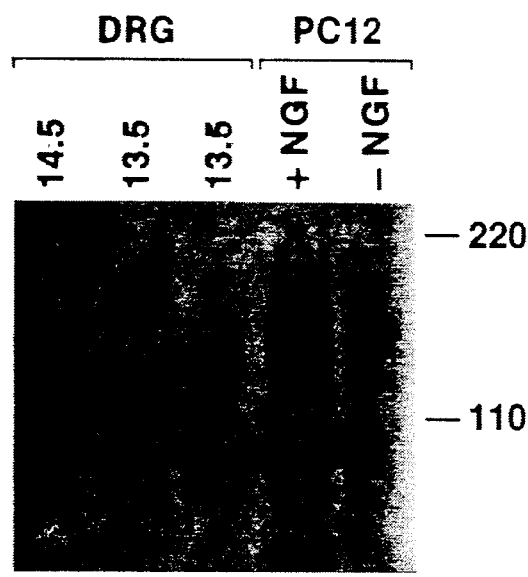
Figure 4B:
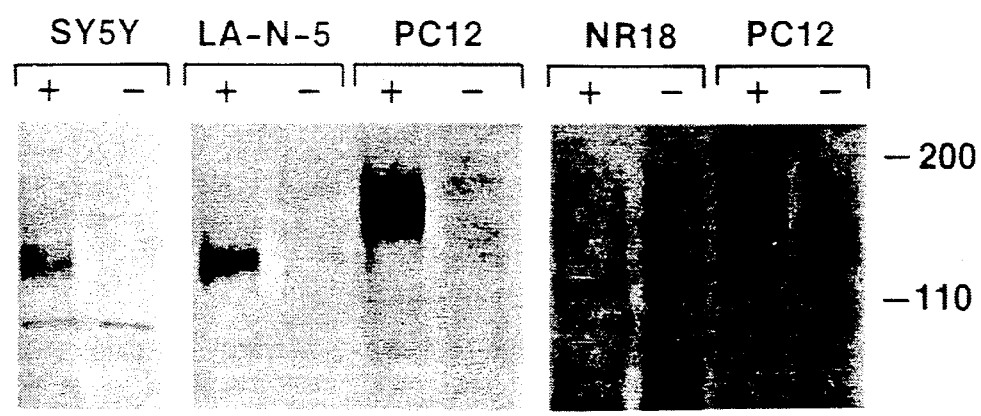

FIG. 4 shows NGF-dependent tyrosine phosphorylation of p140trk in the human neuroblastoma cell lines LA-N-5, SY5Y, and dorsal root ganglia from mouse embryos. FIG. 4*a*, p140trk was immunoprecipitated from untreated (−) or NGF treated (+) LA-N-5 cells (K. H. Sonnenfeld and D. N. Ishii, *J. Neurosci. Res.* 8:375-391 (1982)), SY5Y cells (K. H. Sonnenfeld and D. N. Ishii, (1982)), NR18 cells (M. A. Bothwell et al., *Cell* 21:857-866 (1980)), or PC12 cells. Immunoprecipitates were probed with P-tyr antibodies. The differences in trk protein mobilities are due to differences in glycosylation. FIG. 4*b*, tyrosine phosphorylation of p140trk in DRGs from 13.5 day or 14.5 day embryonic mice. DRGs were maintained in 100 ng/ml NGF for ≧ 10 min prior to lysis and immunoprecipitation with trk antibodies. trk immunoprecipitates were probed with P-tyr antibody. Tyrosine phosphorylated p140trk from NGF-treated (+) PC12 cells or untreated (−) PC12 cells is shown for comparison. Samples were normalized for cell protein. Molecular weight markers in kDa are indicated.

Cell lines were treated with 100 ng/ml NGF for 5 min and p140trk immunoprecipitated as in FIG. 1. DRGs were prepared by dissection for 13.5 or 14.5 day mouse embryos. 100 DRG's were treated with NGF, washed, and subjected to Dounce homogenization in 1% NP40 lysis buffer. Lysates were immunoprecipitated with trk antibody and the trk proteins were analyzed by antiphosphotyrosine immunoblots.

Figure 5:
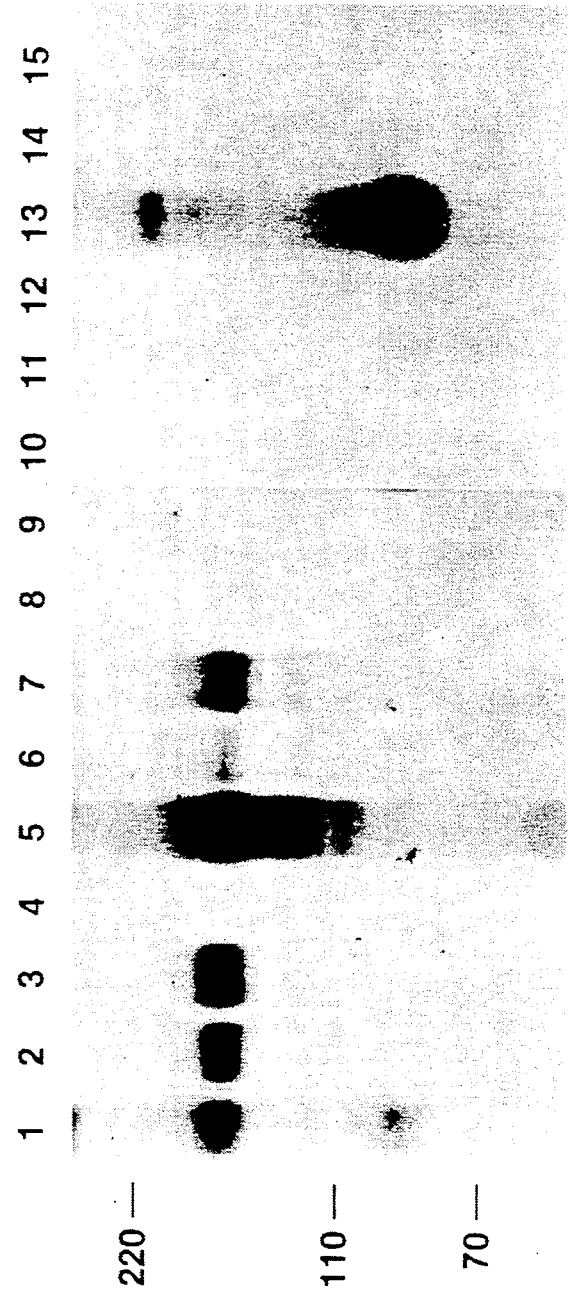

FIG. 5 depicts the affinity crosslinking of NGF to p140trk on PC12 cells and rtrk 3T3 cells. trk receptors were labeled by cross-linking of $^{125}$I-NGF to cultured cells using HSAB. The cell lines analyzed were PC12 cells (lanes 1-4), rtrk 3T3 cells (lanes 5-9), NIH-3T3 cells (lanes 10-11) and A875 human myeloma cells (lanes 13-15). Lysates from cells were immunoprecipitated with anti-NGF (lanes 1, 5, 9-14), p140trk antibody 7-4 which is another trk antibody generated in bacteria against the p70trk oncogene (7-4), (Martin-Zanca, et al., 1988) (lanes 2 and 6), or p140trk antibody 43-4 in the absence (lanes 2, 7 and 15) or presence (lanes 4 and 8) of 10$\mu$g/ml competing trk peptide. Crosslinking was performed in the presence of excess unlabeled NGF (5$\mu$m) in lanes 9, 11, and 14. The antibody 7-4 immunoprecipitates 3-5 fold less p1405.4trk than does antibody 43-4. Molecular weight markers in kDa are indicated.

$^{125}$I-NGF was prepared by lactoperoxidase treatment to specific activies of 2500-3500 cpm/fmole. Crosslinking of p140 trk to $^{125}$I-NGF was performed as previously described (B. L. Hempstead,, *Science* 243:373-375 (1989), 1990)). Cells ($2 \times 10^6$/ml) were incubated with 0.5 nM $^{125}$I-NGF for 2 hr at 4° C. HSAB (50$\mu$M) was added and the reaction exposed to long ultraviolet wavelight for 10 min. After washing in 50 mM lysine in phosphate buffered saline, cells were lysed in buffer containing 1% NP40 and the lysates immunoprecipitated and analyzed on 7.5% SDS-PAGE as described (Kaplan et al., 1990)).

Figure 6B:
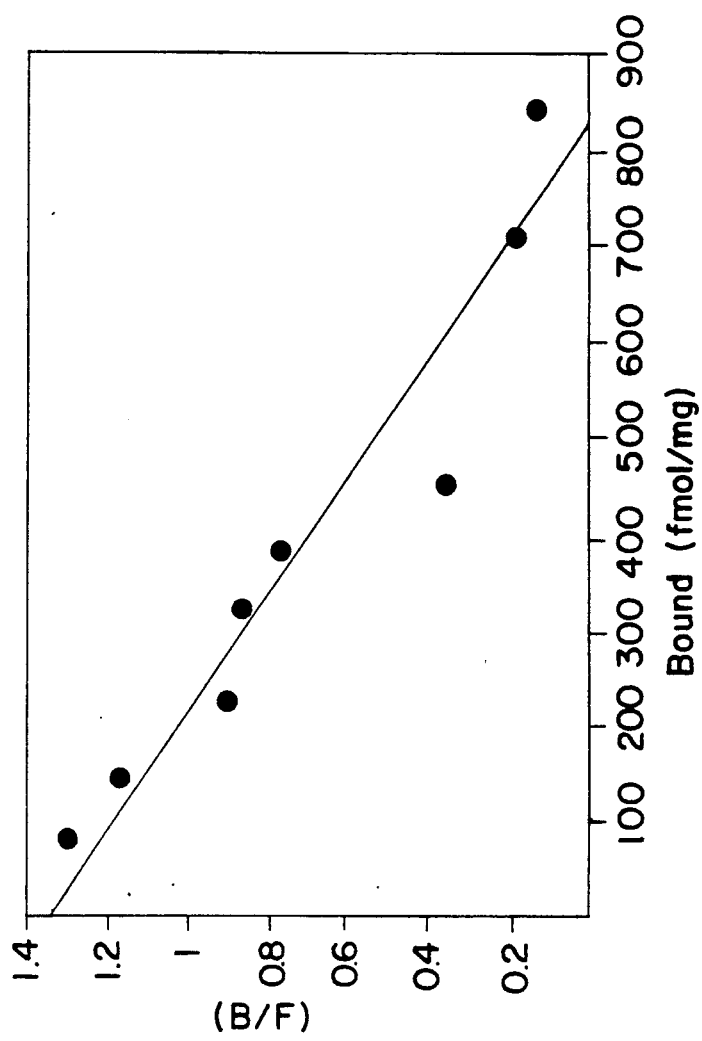
Figure 6A:
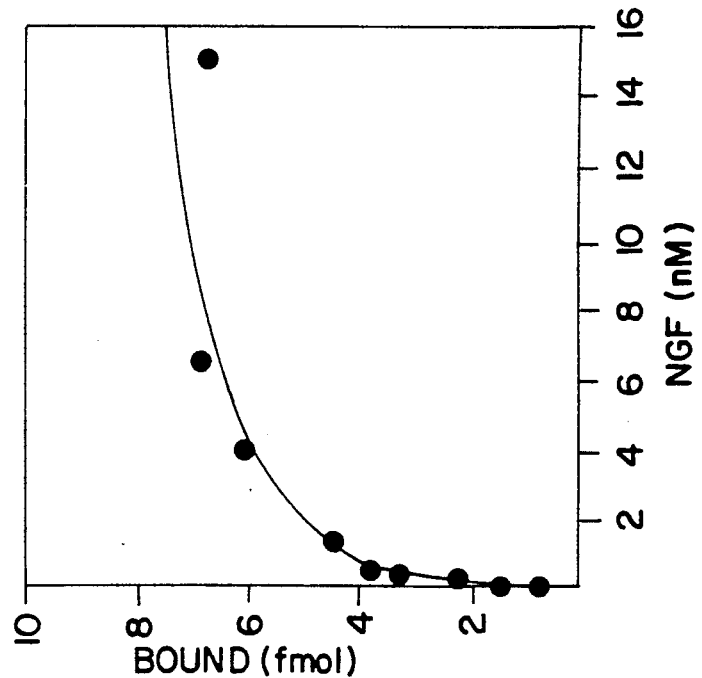

FIG. 6 demonstrates the equilibrium binding analysis of trk receptors in cell membranes prepared from rtrk 3T3 cells. Binding of $^{125}$I-NGF was analyzed in crude membrane preparations by filter binding as described (Hempstead 1989). Reactions were carried out in triplicate in the presence or absence of excess unlabeled NGF with 10 $\mu$g of membrane protein for 1 hr. at 30° C. and filtered under vacuum through Millipore HVPL filters. Over 80% of specific binding was detected after subtracting values obtained in the presence of unlabeled NGF. A) Saturation binding curve; B) Data in (A) plotted according to Scatchard. Only binding values above 50% specific binding were used. The LIGAND program was used to determine Kd.

Figure 7:
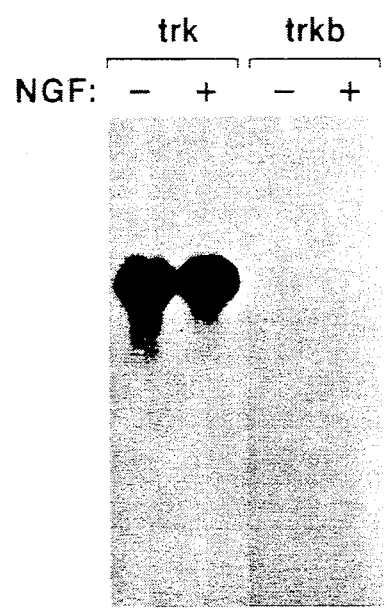

FIG. 7—Northern transfer analysis of trk and trkb transcripts in NGF treated (+) or untreated (−) PC12 cells. RNA preparation and Northern transfer analysis was preformed as described previously (D. Martin-Zanca et al., *Genes Dev.* 4:683-694 (1990)). Cells were treated with 50 ng/ml NGF(+) (Boehringer mannheim Biochemicals) and were harvested 48h latter after differentiation had occured. 20 $\mu$g of total RNA was loaded per lane, and the filter was hybridized with a trk (Martin-Zanca et al., 1990) or trkb (Klein et al., *Development*4:845-850, 1990) specific probe.

DETAILED DESCRIPTION OF THE INVENTION

The present invention relates to a complex comprising nerve growth factor (NGF) and trk-proto-oncogene protein. The present invention further relates to methods of utilizing the complex.

One embodiment of the present invention relates to a complex formed by the interaction of NGF with trk-proto-oncogene protein that is free of protein with which it is naturally associated. The trk-proto-oncogene product is a 140kDa glycoprotein tyrosine kinase and a component of a high affinity NGF receptor.

The present invention relates to detection and quantitation methods that may be used in diagnostics and therapeutics in identifying NGF (ligand), trk-protooncogene protein receptor or the ligand-receeotor complex.

Neurons of the central and peripheral nervous system are dependent on NGF for their continued survival. To date, NGF-dependent neurons that have been identified are sensory neural crest-derived (trigeminal, superior, juglar and dorsal rout ganglia neurons), sympathetic neurons and cholinergic neurons of the basal, media septal and diagonal septal band nuclei of the brain. This last neuronal type are found to be degenerative in Alzheimer's and Huntington's disease.

The knowledge and understanding of NGF-mediated response as occurring via a complex with the trk tyrosine kinase has broad implications for the study of nerve survival, regeneration and accurate diagnosis and potential therapy for neurodegenerative diseases that affect NGF-dependent neurons.

Since NGF-dependent neurons respond via the NGF-trk proto-oncogene tyrosine kinase complex, the methods described herein provide a means for identifying other neuronal types other than those described above which may lead to the identification of other neuronal disorders. In this regard, applicants have recently identified trk expression (and therefore NGF-responsive neurons) in the trigeminal mesencephalic nucleus. These neurons mediate many important sensory functions throughout the brain and may be affected in as yet unidentified neuronal disorders.

The methods of the present invention may also aid in the understanding of the role of the interaction between NGF and its receptor, the trk-proto-oncogene product as a transducer of NGF signals. Considerable expertise and information is available from the past study of tyrosine kinases in other biological systems (i.e., oncogenesis and cell growth) that indicate existing biochemical cascades within the cell that are the signal transducing pathways to the nucleus. Thus NGF binding to trk initiates a signal cascade inside the cell that is amendable to identification, study, and perhaps ultimately, to manipulation, utilizing skills and methodologies that are already in existence.

The present invention further relates to a method of detecting and quantitating trk-protooncogene receptor in a biological sample using labeled NGF as a probe. Suitable labels include, for example, radiolabels such as $^{125}I$, and fluorescein.

Using standard methodologies well known in the art and described herein, a biological sample can be extracted with a non-ionic detergent and incubated with labeled NGF in the presence or absence of unlabeled NGF. The resulting complex can be separated from the uncomplexed (or unbound) labeled material, for example, by immunoprecipitating the complex with a specific polyclonal antibody, for example, the 43-4 or 4.7 rabbit anti-trk antisera and, in parallel, monoclonal phosphotyrosine antibody, such as Ptyr 4G10, for example, that recognizes the trk-proto-oncogene receptor protein or the NGF-trk proto oncogene receptor complex. The overall signal resulting from the presence of label associated with the resulting complex is compared with the signal from a mock sample. The mock sample is prepared using purified trk-proto-oncogene receptor protein in a known quantity treated the same way as the biological sample.

Alternatively, the complex may be separated from uncomplexed material by precipitating with polyethylene glycol. In both methodologies, the amount of label that is immunoprecipitated or precipitated is directly related to the amount of complex in the biological sample.

The present invention also relates to a method for detecting and quantitating NGF in a biological sample using labeled trk-proto-oncogene receptor as a probe. The method is carried out as a reciprocal binding assay following the methodology described above except substituting as antibody, one that specifically recognizes NGF or the NGF-trk-proton-cogene receptor complex. Antibodies against NGF are well known in the art.

The present invention also relates to further methods of detecting and quantitating NGF-trk-proto-oncogene protein receptor complexes in a sample. In one aspect, complexes are detected and quantitated using antibodies directed against NGF, trk-proto-oncogene receptor protein or the NGF-receptor complex. Antibodies can be either polyclonal or monoclonal; examples of both are described above and below in the Example Section. A sample an be extracted with non-ionic detergent and incubated with label NGF or trk-proto-oncogene receptor protein. After incubation, the sample is covalently cross-linked with a lipophilic photoaffinity cross-linking agent for example, HSAB. Chemical crosslinking agents, such as disuccinimidil suberate (DSS) may also be used in this procedure. The sample is immunoprecipitated with specific antibody or precipitated with polyethylene glycol. Quantitation requires chromatographic separation by, for example, gel electrophoresis, followed by autoradiography.

The present invention also relates to diagnostic methodology using the methods described above. The disorders which are diagnosed by the methods of the present invention include, for example, neurodegenerative diseases that affect NGF-dependent neurons such as Alzheimer's and Huntington's diseases. The present diagnostic methods can also be used to measure neuronal disorders in tissue derived from neuronal cell types described previously, which may lead to diagnostics of as yet unidentified neuronal disorders.

The present invention further relates to methods of detecting other trk related receptor and NGF related neurotrophic factor complex using similar methods as those utilized above for detecting the trk/NGF complex. The trk gene is a member of a structurally related gene family of which at present at least three members have been identified (trk, trkb, and trkc). Likewise a growing number of neurotrophic factors are emerging on the basis of similar structure and function to NGF such as BDNF and NT-3 for example. It is very likely that methods used to identify the trk/NGF complex will lead to parallel discoveries with the additional trk and NGF-related genes. The strategies used to identify, characterize and study these trk-related/NGF-related complexes (ie.: trkb/BDNF) will be based on the discovery herein described. Any implications at the practical or therapeutic levels will apply to these neurotrophic factors. The knowledge of trk-related/NGF-related complexes, for example, Trkb/BDNF, will provide insight into the survial capacities of a different subset of nerve cells to those dependant on NGF. Similar assays and strategies previously described to those conceived or devised for detecting the trk/NGF complex would apply to the detection of the related complex for example, use of phosphotyrosine and trkb antibodies for immunoprecipitating trk-related/NGF-related complexes.

The present invention further relates to therapeutic methodologies and the development of detection kits or pharmacological agents that enhance NGF-mediated nerve regeneration or survival. This will depend on the use of trk antibodies and phosphotyrosine antibodies to assay for the quality of the procedure. Most obvious in the area of potential therapeutic value is the development of drugs that either enhance or inhibit tyrosine phosphorylation. Since trk mediates signalling via phosphorylation on tyrosine of messenger molecules, its signalling could be altered as required in cells. These studies would initially be developed and assessed in tissues or cell culture systems prior to any potential application. Drugs would be added to trk-expressing tissue culture cells together with or in the absence of NGF and the state of trk activation, as measured by tyrosine phosphorylation, could be assessed. Progress in developing these drugs would be most effectively monitored with antibodies that recognize trk and/or phosphorylated tryosine. Thus development of any useful therapies in this area will depend on the ability to identify the activation state of trk and/or any of its downstream substrates. Next, animal models (rat or mouse) will be used in which specific nerve connections are disrupted, the promising pharmaceuticals administered, and finally analysis of the sacrificed animals will be performed to assess the regeneration of nerves using trk/ngf or trk-related, NGF-related anitbody assays as described.

The present invention also relates to other therapeutic methods for designing pharmaceuticals that enhance the stimulation of degenerative nerves in diseases such as Alzheimer's and Huntington's.

trk and low affinity NGF receptor 75/cNGF-R are required together for high affinity response to NGF. Methods could be devised that would enhance detection of NGF using the high affinity complex. Knowledge of the existence for a trk/NGF complex could lead to the development of modified NGF molecules that hyperstimulate trk activation. These NGF derivatives might be of importance in the stimulation of degenerating nerves stemming from diseases, for example, Alzheimer's and Huntington's, or from injury.

Many substrates of tryosine kinases have been identified. Identification of trk-specific substrates could lead to discovery of an intermediate molecule in the NGF pathway that can be manipulated pharmalogically to enhance or inhibit NGF-mediated signals.

EXAMPLES

Example 1

Tyrosine phosphorylation of p140$^{prototrk}$ in response to NGF

The stimulation of p140$^{prototrk}$ tryosine phosphorylation in response to NGF addition to PC12 cells is rapid, specific and occurs in the presence of physiological amounts of NGF.

Figure 2A:
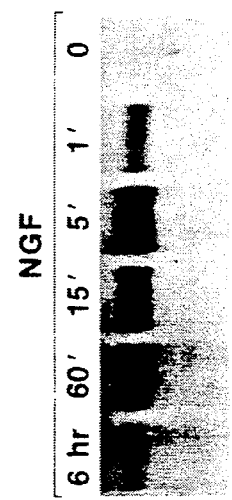
Figure 2B:
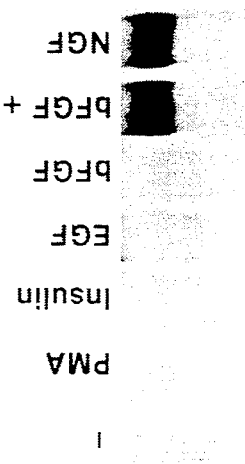
Figure 2C:
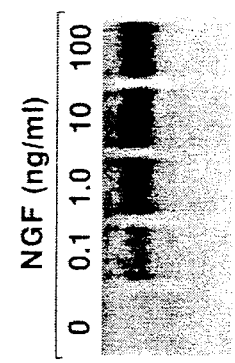

This previous study utilized immunoblotting analysis with phosphotyrosine (P-tyr) antibodies to detect tyrosine phosporylation of p140$^{prototrk}$. To determine if enhancement of serine or threonine phosphorylation of p140$^{prototrk}$ are induced by NGF, and to compare the relative amounts of tyrosine, serine, and threonine phosphorylation, PC12 cells were labeled with $^{32}$P-orthophosphate prior to NGF treatment and immunoprecipitation with antibodies to p140$^{prototrk}$. p140$^{prototrk}$ was phosphorylated predominately on serine residues in immunoprecipitates from untreated cells and cells treated with 50 ng/ml NGF for 5 min. The presence of NGF, however stimulated thr tyrosine phosphorylation of p140$^{prototrk}$ 20-fold, although this represented less than 5% of the newly incorporated phosphate residues. In contrast, p140$^{prototrk}$ was labeled predominantly on tyrosine in immune complex kinase assays from NGF-treated PC12 cells or in $^{32}$P-labeled NIH-3T3 cells transfected with the rat trk gene (rtrk-3T3) (FIG. 1a). The tyrosine phosphorylation of p140$^{prototrk}$ expressed in NIH-3T3 cells was constitutive, apparently due to autocrine stimulation by NGF produced by these cells. treatment of rtrk-3T3 cells with suramin, a polyanionic compound which inhibits and reverses the binding of some growth factors to their receptors (M. Hosang et al., *J. Cell. Biochem.* 29:265–273 (1985)), markedly reduced the tyrosine phosphorylation of p140$^{prototrk}$ in vivo and in immune complex kinase assays (FIG. 1b). when NGF was added to the suramin treated cells for 10 min, tyrosine phosphorylation of p140$^{prototrk}$ observed in vivo and invitro was stimulated at least 10-fold (FIG. 1b).

trk tyrosine phosphorylation occured within one minute of NGF treatment cells, reached maximum levels after five minutes, and declined thereafter (FIG. 2a). Residual phosphorylation was detected after two days of treatment with NGF when the cell population was fully differentiated. trk tyrosine phosphorylation was also specific to NGF. Other peptide growth factors that elicit tyrosine phosphorylation in PC12 cells were tested in our assay (V. Hamburger and R. Levi-Montalcini, *J. Exp. Zool.* 111:457–502 (1949) I. B. Black et al., Growth Factors and Development, Current Topics in Developmental Biology, vol. 24: (ed. Nilsen-Hamilton, M.) 161–192 1990)). EGF, basic FGF, insulin, and the phorbol ester PMA failed to induce trk was seen in cells treated with both basic FGF and NGF (FIG. 2b). It has been previously shown that these agents produce similar patterns of early responses in PC12 cells, including transcriptional activation of c-fos and cmyc (R. Levi-Montalcini and B. Booker, *Proc. Natl. Acad. Sic.* USA 46:384–391 (1960)). However, of these factors, only NGF and basic FGF stimulate neurite outgrowth.

To determine the minimal concentration of NGF capable of eliciting trk tyrosine phosphorylation, a dose response experiment was performed. Tyrosine phosphorylation was half maximal at 0.1 ng/ml NGF (50 pM) (FIG. 2c) indicating the trk phosphorylation occurs at physiologically relevant concentrations of NGF (S. Cohen, *Proc. Natl. Acad. Sci. USA* 46:302–311 (1960)).

Example 2

Expression of trk gene in embryonic sensory neural crest-derived neurons

The trk gene is expressed in embryonic sensor neural crest-derived neurons including dorsal root ganglia (DRG) (FIG. 3 and Martin-Zanca et al. 1990). This expression is confined to neurons (note that the darkly staining glial cells are devoid of silver grains) and maintained in the adult. To determine wther the trk protein in embryonic neurons was responsive to NGF, DRG from E13.5 and E14.5 mouse embryos were explanted, maintained in 50 ng/ml NGF on ice≧10 mm., lysed, and subjected to trk antibody precipitation and anti-ptyr immunoblotting analysis. As shown in FIG. 3A, phosphorylation of the p145$^{prototrk}$ was detectable in 14.5 day DRG but not in two independent preparations of 13.5 day DRG. Tyrosine phosphorylated trk protein was not detectable in the absence of exogenously administered NGF.

Dissection of DRG provides primarily the cell bodies and eliminates the axons, therefore the significance of these data with regard to timing and degree of p145$^{prototrk}$ activation should be interpreted with caution. The results in 14.5 DRG, however, determine that freshly dissected embryonic DRG neurons contain trk protein which is phosphorylated in response to NGF.

Example 3

NGF stimulates p140$^{prototrk}$ tyrosine phosphorylation in several trk-expressing cell types To determine whether phosphorylation of p140$^{prototrk}$ in response to NGF was unique to rat PC12 cells or occurred in other NGF responsive cell lines, the state of the trk protein in additional neuroblastoma cell lines from different species was assayed. It was observed that p140$^{prototrk}$ tyrosine phosphorylation was also enhanced by NGF in the human neuroblastoma cell line LA-N-5 and in the murine cell line SY5Y (FIG. 4b). LA-N-5 and SY5Y cells express 4-fold less trk mRNA than PC12 cells, accounting for the lower amounts of tyrosine phosphorylated trk observed in these cell lines compared to PC12 cells.

Derivatives of the PC12 cell line have been generated by mutagenesis that have lost high affinity response to NGF (Bothwell et al. 1981). One such line, NR18, lacks 75kNGF-R. Introduction of 75kNGF-R into these cells resulted in the reconstitution of biphasic scatchard profile and at least partial function reconstitution (Hempstead et al. *J. Biol. Chem.* 265:9595-9598 (1990)). NR18 cells express the trk proto-oncogene at greatly reduced levels (see Hempstead et al. 1991).

The Applicants next analyzed the phosphorylation state of the trk receptor on the NR18 cell line that has greatly reduced responsiveness to NGF (Bothwell et al., *Cell* 21:857-866 (1980)). Consistent with RNA expression data (see Hempstead et al. 1991) no phosphorylation of p140$^{prototrk}$ in response to NGF was observed in these cells (FIG. 4b). Thus, in NR18 cells, the tyrosine phosphorylation of p140$^{prototrk}$ correlates with the reduced ability of NGF to elicit a biological response.

Example 4

Trk receptor directly binds to NGF

The above results, demonstrating the rapid phosphorylation of p140$^{prototrk}$ in several trk-expressing cell lines treated with NGF, suggested that the trk receptor might directly bind NGF. To determine if NGF was capable of binding to p140$^{prototrk}$, several cell lines were analyzed for the ability of trk-specific antisera to precipitate receptor-ligand complexes in affinity crosslinking experiments (FIG. 5). The cell lines assayed were rat PC12, human LA-N-5, mouse SY5Y, mouse NIH-3T3, mounse rtrk-3T3, and human AB75 cells. NGF induces the tyrosine phosphorylation of p140$^{prototrk}$ in PC12, LA-N-5, SY5Y, and rtrk-3T3, but not in AB75-melanoma or NIH-3T3 cells which express no detectable trk messenger RNA. $^{125}$I-labeled NGF was crosslinked to cells using the lipophilic photoaffinity agent HSAB. Previous studies with this crosslinking agent have shown that in PC12 cells and sympathetic neurons, two NGF containing species of 100 kDa and 150-160 kDa are observed (J. Massague et al., *J. Biol. Chem.* 256:9419-9424 (1981); Hempstead, et al. 1990; S. O. Meaking and E. M. Shooter, *Neuron* 6:153-163 (1991)). The 100 kDa species represents $^{125}$I-NGF bound to 75kNGF-R (M. Hosang and E. M. Shooter, *J. Biol. Chem.* 260:655-662 (1985)). Following crosslinking, the cells were washed to remove unbound $^{125}$I-NGF, lysed in detergent, and the lysates incubated with antibodies (FIG. 4). It was observed that the 160 kDa species in anti-NGF or anti-p140$^{prototrk}$ immunoprecipitates from PC12 and rtrk-3T3 cells, and not in A875 or IH-3T3 cells. The immunoprecipitation of the 160 kDa species was blocked by addition of a trk-derived peptide used to generate the antibody, and was not seen if excess unlabeled NGF was added to the $^{125}$I-NGF treated cells prior to crosslinking. A 160 kDa crosslinked product was also observed in LA-N-5 and SY5Y cells. The crosslinked 100 kDa species were present in PC12 and A875 cells and not in the 3T3 cell lines, reflecting the absence of expression of the 75kNGR-R in NIH-3T3 cells. The above experiments establish that NGF binds to p140$^{prototrk}$ and that this binding is seen only in cell lines which show p140$^{prototrk}$ tyrosine phosphorylation in response to NGF.

Of equal importance to the demonstration of binding, it is essential to determine whether the affinity of binding reflects physiologically relevant conditions. Scatchard plot analysis was carried out to determine that affinity of NGF for p140$^{prototrk}$ expressed in NIH-3T3 cells. Crude membranes were prepared from cells and assays by binding to $^{125}$I-NGF. Membranes obtained from rtrk-3T3 cells displayed a linear Scatchard plot with a Kd of approximately $10^{-9}$M (FIG. 6). By this analysis, the number of receptors was approximately 200,000-500,000/cell.

Example 5

Expression of trk or trk-related messenger RNA in several cell types

The trk gene is a member of a gene family of TK receptors that includes the related gene trkb. To determine if trk is transcribed in PC12 cells, the expression of trk transcripts was assayed by Northern transfer analysis with a full-length trk cDNA probe (R. Klein et al., Development 4:845-850 (1990). PC12 cells contained trk transcripts (FIG. 7). The level of trk transcripts was not affected by the addition of NGF. To determine whether additional trk-related genes were transcribed in PC12 cells, mRNA was hybridized at low stringency with the highly conserved trk Tk domain. trk transcripts have been found in LA-N-5 cells, Sy5y cells and DRG from 13.5 day or 14.5 day embryonic mice. trkb expressing cell lines, as determined by mRNA analysis will help determine the next steps in interactions with trkb ligand (BDNF).

While the foregoing invention has been described in some detail for purposes of clarity and understanding, it will be appreciated by one ⌣killed in the art from a reading of this disclosure that various changes in form and detail can be made without departing from the true scope of the invention.

What is claimed is:

1. A method of detecting a neurotrophic agent with reference to a control, comprising the steps of
   (a) bringing cells that express a trk-proto-oncogene receptor protein into contact with a putative neurotrophic agent, wherein said contact is effected under conditions such that binding of said neurotrophic agent to and subsequent activation of said receptor protein can occur, (b) determining an amount of tyrosine phosphorylation of trk-proto-oncogene receptor protein effected by step (a), (c) comparing said amount of phosphorylation determined by step (b) with that of a control trk-protooncogene receptor which is not contacted with said putative neurotrophic agent, whereby an increase in said amount relative to that of said control detects said agent as neurotrophic.

2. A method according to claim 1 further comprising, prior to step (a), the step of bringing said cells into contact with orthophosphate, and in step (b), contacting trk-protoooncogene receptor protein with anti-trk antibody to effect immunoprecipation and measuring the amount of 3-orthophosphate incorporated in immunoprecipitated trk-proto-oncogene receptor protein, whereby said measuring determines an amount of tyrosine phosphoylation of trk-proto-oncogene receptor protein effected by step (a).

3. A method of detecting nerve growth factor in a sample, comprising the steps of
   (a) contacting a trk-proto-oncogene receptor protein with a biological sample suspected of containing nerve growth factor, wherein said contacting is effected under conditions such that binding between nerve growth factor and trk-proto-oncogene receptor protein can occur,
   (b) determining an amount of tyrosine phosphorylation of the trk-photo-oncogene receptor protein effected by step (a), whereby an increase in said amount of phosphorylation of trk-photo-oncogene receptor protein as compared to the amount of phosphorylation of trk-proto-oncogene receptor protein measured in the absence of nerve growth factor indicates the presence of nerve growth factor in said sample.

4. A method according to claim 3, further comprising the steps of
   (i) after step (a), contacting the sample with an antibody specific for trk-proto-oncogene receptor protein and
   (ii) immunoprecipitating said trk-photo-oncogene receptor protein.

5. A method of detecting an agent that enhances nerve growth factor activity relative to that of a control, comprising the steps of
   (a) bringing cells that express a trk-proto-oncogene receptor protein into contact with a putative nerve growth factor enhancing agent in the presence of nerve growth factor, wherein said contact is effected under conditions such that binding and activation of said recceptor protein can occur,
   (b) determining an amount of tyrosine phosphorylation of trk-proto-oncogene receptor protein effected by step (a),
   (c) comparing said amount of phosphorylation determined by step (b) with that of a control trk-photo-oncogene receptor protein which is contacted with nerve growth factor in the absence of said agent, whereby an increase in said amount of tyrosine phosphorylation relative to that of said control detects said agent as a nerve growth factor enhancer.

* * * * *